United States Patent [19]

Santorilla

[11] 3,998,102
[45] Dec. 21, 1976

[54] SUPPORT SYSTEM FOR A GAS SAMPLER
[75] Inventor: George M. Santorilla, Dearborn, Mich.
[73] Assignee: Clayton Environmental Consultants, Inc., Southfield, Mich.
[22] Filed: Feb. 17, 1976
[21] Appl. No.: 658,572
[52] U.S. Cl. .......................................... 73/421.5 R
[51] Int. Cl.² ............................................ G01N 1/22
[58] Field of Search ... 73/421 R, 421.5 R, 421.5 A, 73/422

[56] References Cited
UNITED STATES PATENTS

| 1,494,855 | 5/1924 | MacMichael | 73/421.5 A |
| 3,832,904 | 9/1974 | Dreuw et al. | 73/421.5 A |
| 3,921,458 | 11/1975 | Logan | 73/422 R |

Primary Examiner—S. Clement Swisher
Attorney, Agent, or Firm—Brumbaugh, Graves, Donohue & Raymond

[57] ABSTRACT

A support system for a gas sampler for collecting samples of gas from a plurality of laterally arranged ports and including a support rail extending outwardly from the ports to support the gas sampler for movement toward and away from said ports, an auxiliary support for the outer end of the supporting rail, a pair of laterally extending tracks and slidable couplings connecting the ends of the rail and auxiliary support to the tracks to facilitate moving the gas sampler from port to port.

6 Claims, 6 Drawing Figures

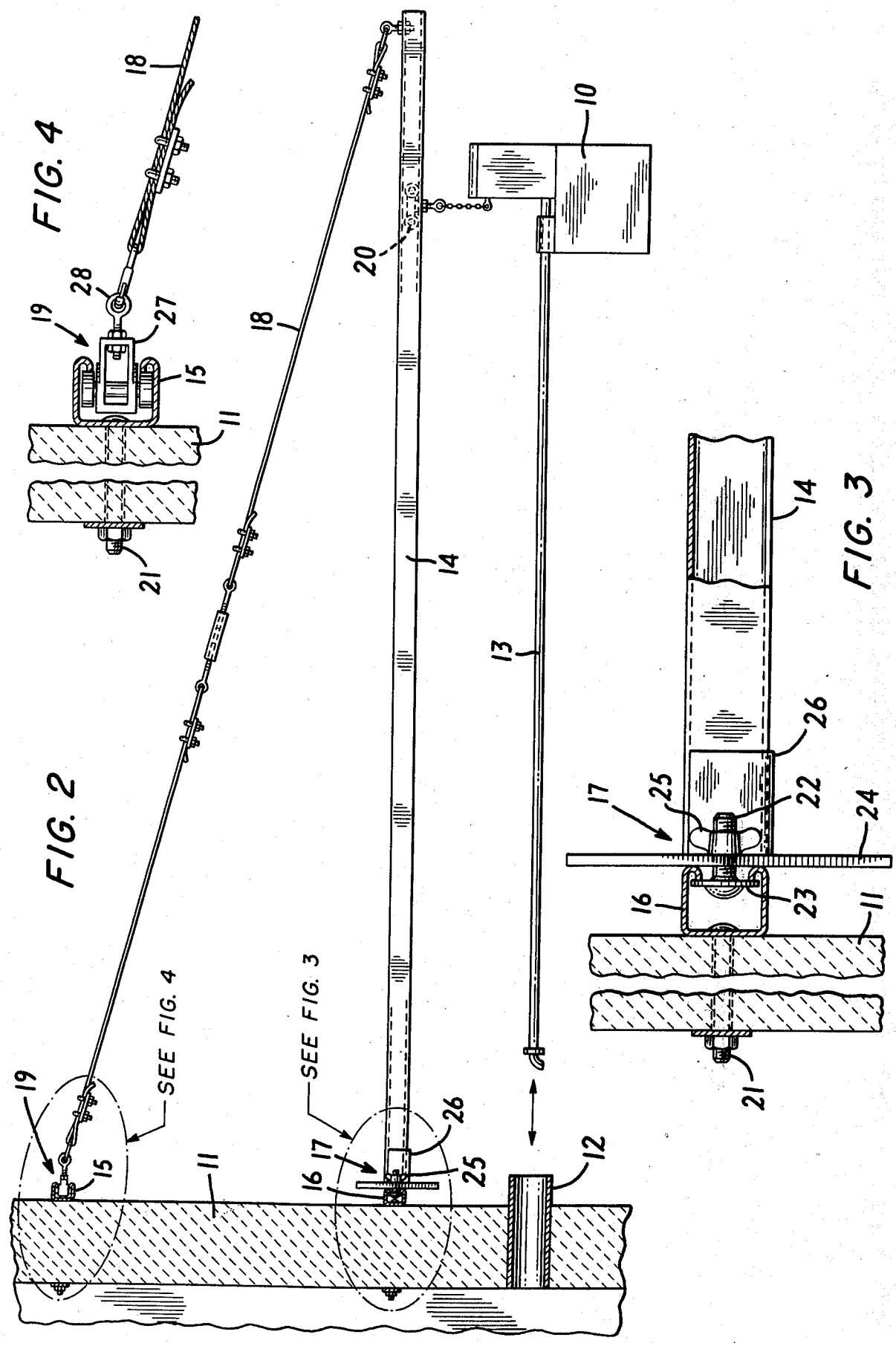

U.S. Patent Dec. 21, 1976 Sheet 3 of 3 3,998,102
FIG. 5
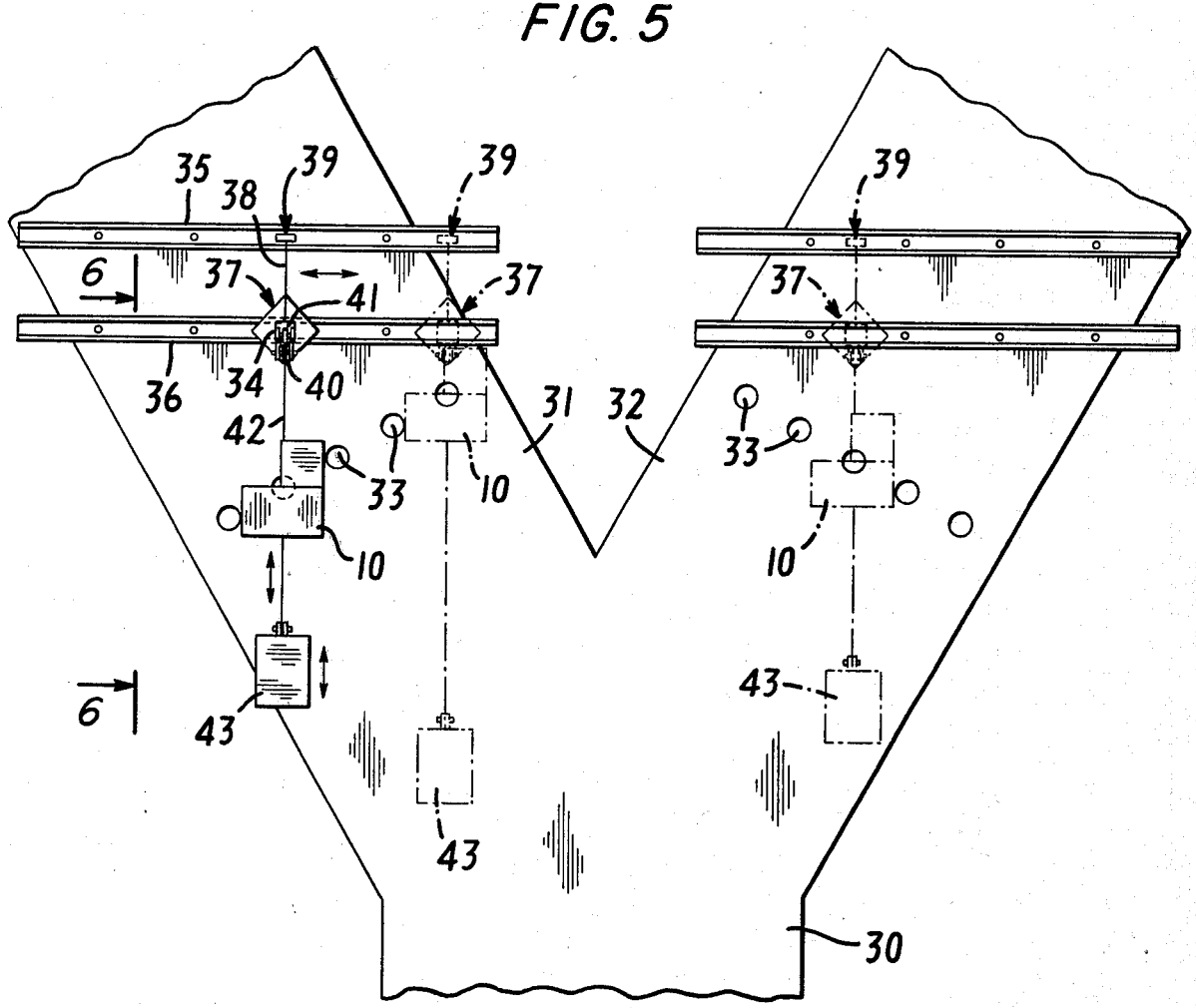
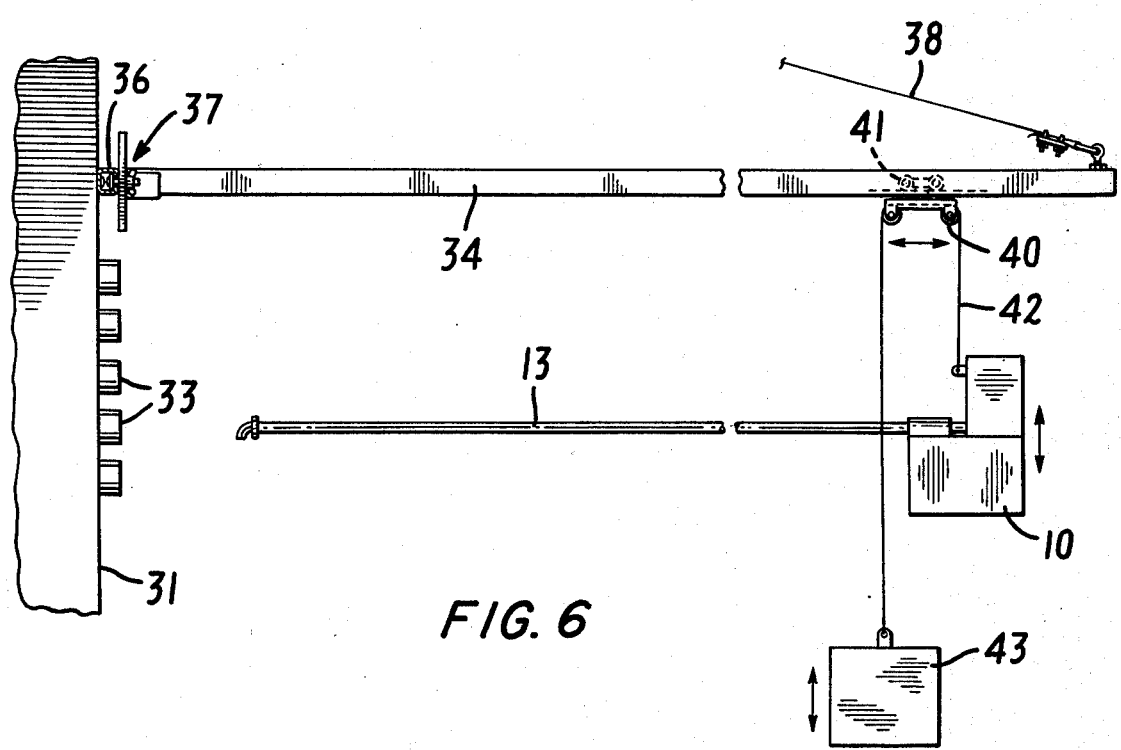
FIG. 6

3,998,102

SUPPORT SYSTEM FOR A GAS SAMPLER

BACKGROUND OF THE INVENTION

This invention relates to gas samplers of the type used for collecting samples of gas from ports in furnaces, smokestacks and industrial gas conduits, and more particularly to a novel support system for a gas sampler to permit it to be moved toward and away from a port and to be moved laterally from one port to another.

Gas samplers of this type have been used in air pollution control for periodically checking and analyzing the pollution materials and pollution content of gases released to the atmosphere. The collection of gas samples is particularly difficult in the case of high stacks which vary greatly in size, altitude and location. To facilitate taking gas samples from the ports of tall stacks, the operator must rig the support system from whatever platform is available at the site.

The support systems heretofore available have included a track for supporting the gas sampler for movement toward and away from a port from which the sample is taken and various means for supporting the track, including an angular brace, a depending leg suport and an overhead guy wire. The track and the guy wire or brack have been mounted directly to the stack. Frequently the testing procedure requires taking samples from a plurality of laterally arranged ports and this requires setting up and taking down the support system at each port.

The object of the present invention is to provide an improved support system which can be easily and quickly set up and taken down and, when set up, can be utilized to take samples from a plurality of laterally spaced ports, thereby making the testing procedure more efficient and less hazardous.

The support system of the present invention includes a support rail extending outwardly from the surface accommodating the ports to support the gas sampler for movement toward and away from the ports, an auxiliary support for the outer end of the supporting rail, a pair of laterally extending tracks mounted to the wall accommodating the ports and slidable couplings connecting the ends of the rail and auxiliary support to the tracks to facilitate moving the support rail and auxiliary support from port to port. The support system of the present invention can be set up and shifted from port to port to take a plurality of samples before the support system is taken down.

For a complete understanding of the present invention reference can be made to the detailed description which follows and to the accompanying drawings in which:

FIG. 2 is a view taken along the line 2—2 of FIG. 1 looking in the direction of the arrows;

FIG. 3 is an enlarged view, partly in cross-section, of a portion of the support system shown in FIG. 2;

FIG. 4 is an enlarged view, partly in cross-section, of a portion of the support system shown in FIG. 2;

FIG. 5 is an elevational view showing an alternative form of the support system of the present invention; and FIG. 6 is a view taken along the line 6—6 of FIG. 5 looking in the direction of the arrows.

Figure 1:
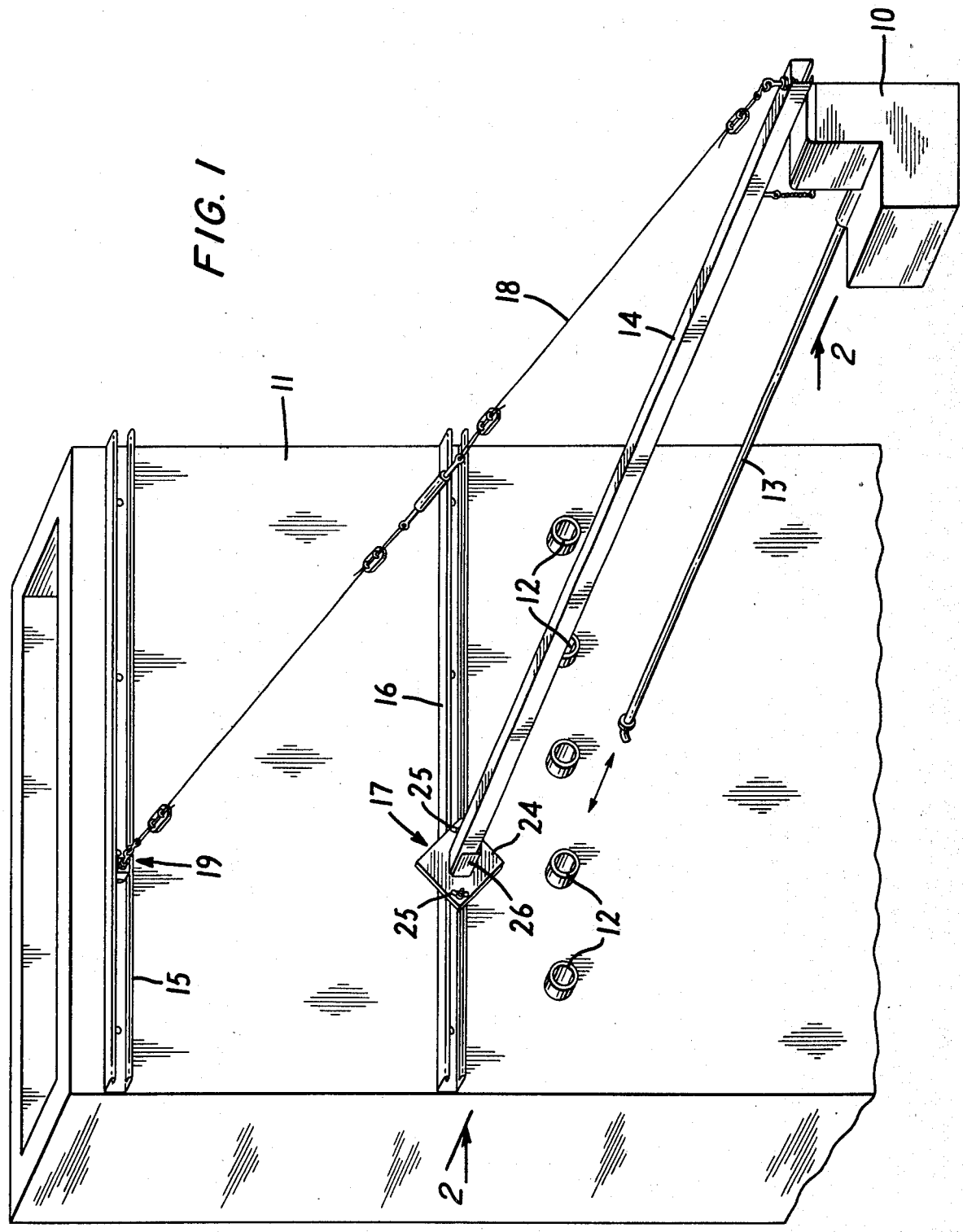
FIG. 1 is an isometric view of the support system of the present invention.

Referring to FIGS. 1 and 2 of the drawings, a gas sampling device 10 is shown supported by the support system of the present invention on the side of a smokestack 11 containing a plurality of ports 12 spaced laterally along a side of the stack. A probe 13 of the gas sampling device is introduced seriatim into the ports to collect samples of the gas at each location so that these samples can be analyzed for pollutant materials. The sampler and probe are conventional devices which do not constitute part of the present invention.

The support system of the present invention includes a support rail 14 extending outwardly from the wall for supporting the gas sampler for movement toward and away from the wall, a pair of laterally extending tracks 15 and 16 mounted to the wall, a slide coupling 17 connecting the inner end of the supporting rail for lateral movement along the track 16, an auxiliary supporting guy wire 18 connecting the outer end of the rail 14 to the track 15 and a slide coupling 19 for moving the upper end of the guy wire laterally along the track 15.

The rail 14 is a channel-like member accommodating therein a rolling trolley 20 from which the sampler 10 is suspended.

The upper and lower laterally extending tracks 15 and 16 are also channel-like members which permit lateral adjustment of the slide couplings 17 and 19 to permit the sampler to be moved from port to port. The tracks 15 and 16, as best shown in FIGS. 3 and 4, are connected by bolts 21 to the wall of the smokestack.

The coupling 17 includes bolts 22 having enlarged heads 23 retained within the channel and a plate 24 through which the bolts 22 pass so that the plate can be locked against the outside of the channel by nuts 25. The outer surface of the plate 24 carries a support 26 for the inner end of the support rail 14, and the support 26 and support rail are preferably permanently welded together. When the nuts 25 are loosened the coupling can be slidably moved along the track 16 from one port to the next and then locked in place by tightening the nuts.

The coupling 19 includes a rolling trolley 27 accommodated within the channel 15. The trolley carries an eyebolt 28 for connecting the guy wire 18 to the trolley.

An alternative embodiment of the support system of the present invention is shown in FIGS. 5 and 6 in which a gas sampler 10 is shown supported from each leg 31 and 32 of a Y-shaped stack 30. By virtue of the angle of each leg of the stack, the laterally arranged ports 33, which are equally spaced from the discharge ends of the stacks, are also at different heights. The support system for use in this application includes a support rail 34 extending outwardly from the wall of the stack, a pair of laterally extending tracks 35 and 36 extending laterally along the wall, a slide coupling 37 connecting the inner end of the supporting rail 34 for lateral movement along the lateral track 36, an auxiliary guy wire support 38 connecting the outer end of the rail 34 to the upper laterally extending track 35 and a slide coupling 39 connecting the guy wire support to the laterally extending track 35. The slide couplings 37 and 39 are the same as the corresponding couplings 17 and 19.

The sampler 10 is supported from a pulley wheel system 40 carried by a trolley 41 which travels longitudinally along the rail 34. The sampler is suspended from a flexible cable 42 which loops around the pulley system and is connected with a counterweight 43 at the opposite end thereof to enable the sampler to be adjusted as to height.

In the utilization of the support system of the present invention, the laterally extending tracks 15 and 16 in the embodiment illustrated in FIGS. 1 through 4 of the drawings and the laterally extending channel tracks 35 and 36 in the embodiment illustrated in FIGS. 5 and 6 of the drawings are permanently mounted to the stack walls above platforms accessible to the operator. The sampler, the supporting rail and the guy wire can be carried to the platform or some or all of these components can be stored on the platform. The operator can readily set up the supporting system relative to one port, and after taking a gas sample, he can easily adjust the slidable couplings for the sampler support and the guy wire to an adjacent port for the next sampling. In the case of the embodiment illustrated in FIGS. 5 and 6 of the drawings, the operator can also readily adjust the height of the sampler for each port from which a sample is to be taken.

The invention has been shown in preferred forms and by way of example only, and many modifications and variations may be made therein within the spirit of the invention. For example, the support system of the present invention is shown applied to a rectangular stack, but it can be used with various shapes of stacks. The invention, therefore, is not to be limited to any particular form or embodiment except in so far as such limitations are set forth in said claims.

I claim:

1. A support system for suspending a gas sampler from a wall having a plurality of laterally spaced ports from which samples are to be taken comprising a support rail extending outwardly from the wall for supporting the gas sampler for movement toward and away from the wall, an auxiliary support extending outwardly from the wall and connected to the support rail at a distance remote from the wall, a pair of laterally extending tracks mounted to the wall for the support of the rail and auxiliary support and slidable couplings connecting the wall ends of the rail and the auxiliary support to the tracks to permit the gas sampler to be moved from port to port.

2. A support system as set forth in claim 1 in which at least one of the tracks in channel-shaped to retain at least part of one of the slidable couplings and including means carried by the slidable coupling for locking the slidable coupling in a fixed position relative to the track.

3. A support system as set forth in claim 1 in which at least one of the tracks is channel-shaped to retain a rolling trolley within said channel and means connecting said trolley to the auxiliary support.

4. A support system as set forth in claim 1 in which one of the tracks is disposed above and parallel to the other of said tracks and in which the auxiliary support is a guy wire connecting the end of the support rail remote from the wall to the slidable coupling accommodated in the upper of said tracks.

5. A support system as set forth in claim 1 in which at least one of the laterally spaced ports is at a different height from an adjacent port and including means for suspending the gas sampler from the support rail and means for adjusting the height of the gas sampler through the suspension means.

6. A support system as set forth in claim 1 in which at least one of the laterally arranged ports is at a different height from an adjacent port and including a trolley accommodated for movement along said support rail, a pulley carried by the trolley, a counterweight for balancing the weight of the gas sampler and a flexible connection between the gas sampler and the counterweight which loops around the pulley for the suspension of the gas sampler and the counterweight.

* * * * *